United States Patent [19]

Lewin et al.

[11] 4,028,465
[45] June 7, 1977

[54] ASSAY METHOD FOR SERUM FOLATE

[75] Inventors: Nathan Lewin, Corte Madera; Emmy Tong-In Wong, Moraga, both of Calif.

[73] Assignee: Bio-Rad Laboratories, Richmond, Calif.

[22] Filed: Nov. 10, 1975

[21] Appl. No.: 630,249

[52] U.S. Cl. .................................. 424/1; 23/230 B; 23/230.6; 260/251.5
[51] Int. Cl.² ............... C07D 475/00; G01N 31/06; G01N 33/16; G01T 1/16
[58] Field of Search ........... 23/230 B, 230.3, 230.6; 424/1, 1.5

[56] References Cited

UNITED STATES PATENTS 3,442,819    5/1969    Herbert et al. .................... 252/428

OTHER PUBLICATIONS

Akerkar et al., "Stability of Tritiated Folic Acid used in Radioimmunoassay", Clinical Chemistry, vol. 21, No. 7, p. 1030 (June 1975).

*Primary Examiner*—Joseph Scovronek
*Attorney, Agent, or Firm*—Townsend and Townsend

[57] ABSTRACT

Serum folate assay procedure by competitive binding in which serum folate is stabilized while being freed from serum folate proteins in the presence of a dithiopolyol, preferably a 1,4-dithiotetritol such as dithiothreitol. Subsequently in the procedure, free folate is separated from competitively bound folate by the addition of dry dextran coated charcoal in a tablet form.

15 Claims, 1 Drawing Figure

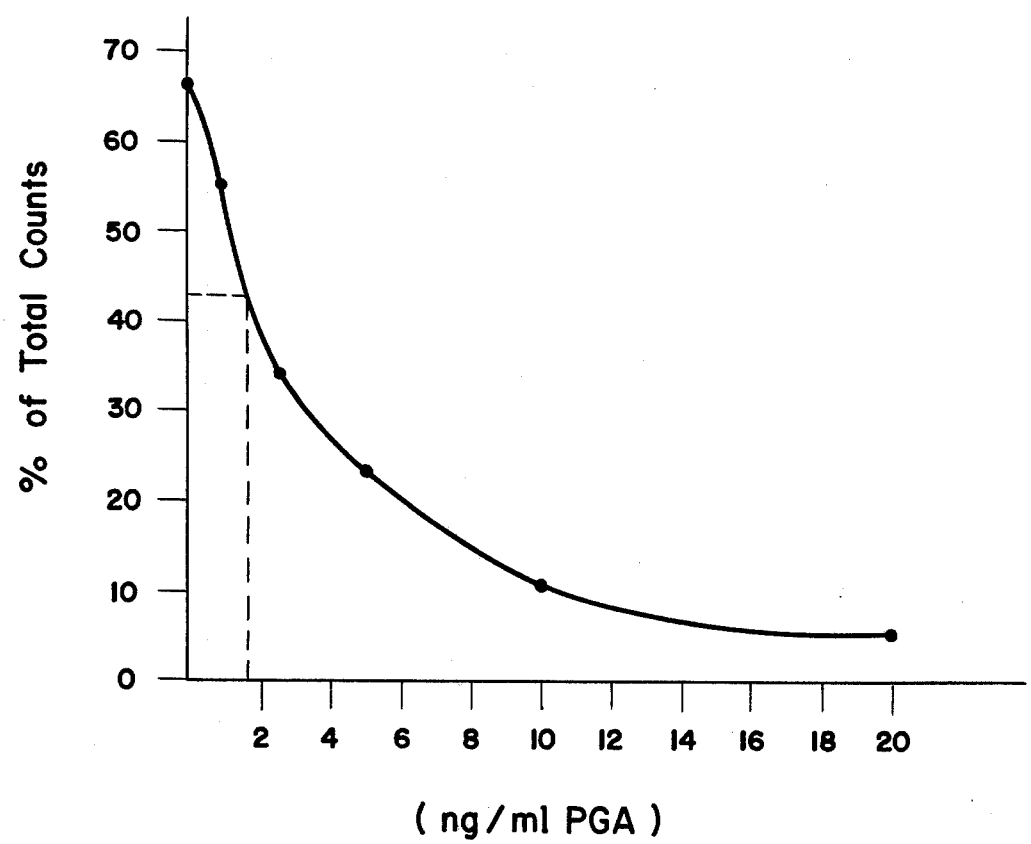

ASSAY METHOD FOR SERUM FOLATE

This invention relates to an assay procedure for serum folate. More particularly it relates to improved stabilizers for use in such an assay, as well as the technique for separating free from competitively bound folate during the assay procedure.

Folate assay procedures based on the competitive binding technique are known, and several such procedures are available commercially. In a folate competitive binding assay a measured amount of patient serum is mixed with a folate protecting buffer and a radioactively labelled folate $^{125}$I (pteroylglutamic acid - "PGA") derivative. Under the influence of heat, folate binding proteins are inactivated while the protective agent stabilizes the folate.

The mixture is then incubated with a measured amount of binding protein. An example is the folate selective preparation of β-lactoglobulin. The amount of the material used is sufficient to bind some, but not all, of the labelled and unlabelled folate present in the mixture. During incubation, the labelled and unlabelled folate compete for the available binding sites of the binding protein on the basis of their concentrations. The more unlabelled folate the sample contains, the less labelled folate will bind to the binding protein. Following incubation the bound folate and unbound or free folate are separated. The degree to which the binding of labelled folate is inhibited by the unlabelled folate present in the serum sample is then determined, and unknown concentration determined from a standard curve.

Previous procedures have utilized mercaptoethanol as a stabilizer in the protecting buffer while inactivating endogenous folate binding proteins by appropriate treatment such as heating. Mercaptoethanol is an evil smelling liquid and is generally undesirable in clinical laboratory procedures of the present type. Ascorbic acid, frequently used as serum-folate preservative, may fulfill similar functions.

Later in the assay, prior procedures have utilized aqueous suspensions of dextran coated charcoal for separating bound folate and unbound or free folate following incubation and competitive binding. Dextran coated charcoal suspensions suitable for use in such separations are disclosed in U.S. Pat. No. 3,442,819 issued May 6, 1969 to V. Herbert.

In accordance with the present invention an assay for serum folate by the competitive binding technique is provided in which serum folate binding proteins are inactivated by heat prior to the competitive binding step. The improvement provided by this invention is inclusion of a buffered solution containing a dithiopolyol stabilizer to be used in the heating step. Preferred stabilizers are 1,4-dithiotetritols, including both of the isomers dithiothreitol and dithioerythritol. It has been found that such dithiopolyols provide the desired stabilization of serum folates when present in a buffered solution having a pH of about 7-10. The present stabilizers are advantageous relative to the previously used liquid mercaptoethanol by virtue of being easily weighed solids with only a mild odor so that they are superior in manipulation and convenience.

The efficacy of the present dithiopolyol is surprising in view of the previous report that dithiothreitol had a harmful effect on folate stability. See Akerkar and Rutner, "Stability of Tritiated Folic Acid Used In Radioimmunoassay,", *Clinical Chemistry*, Vol. 21, No. 7, P. 1030 (1975).

It is noted that 1,4-dithiotetritols have previously been utilized in non-analogous ways. See for example, W. W. Cleland, "Dithiothreitol, A New Protective Reagent For SH Groups", *Biochemistry*, Vol. 3, p. 480 (1964). Dithiothreitol has also been used in a competitive binding radioimmunoassay for angiotensin, as reported in "Competitive Binding Activity of Angiotensin II Analogues in an Adrenal Cortex Radioligand-Receptor Assay", Endo. Vol. 97, No. 2, p. 275 (1975); and "Properties of Angiotensin II Receptors in the Bovine and Rat Adrenal Cortex", *J. Bio. Chem.*, Vol. 249, No. 3, pp. 825–834 (1974).

In another aspect of the present assay, improvements by way of simplicity and reproducibility are obtained by utilizing dextran coated charcoal in dry solid form, as a tablet made from a compressed combination of dextran coated charcoal and an inert binder. In this improved physical form the dextran coated charcoal is used differently from the slurry or suspension as described in the above referenced U.S. Pat. No. 3,442,819. In accordance with the present invention it has been found that the dry, tableted form may be utilized with success, wherein the dry dextran coated charcoal is added in an amount of about 7.5–15 mg, preferably 10 mg, for each .1 ml of serum sample.

In the preferred embodiment the present assay utilizes a radioactive folate tracer. While any suitable radioactive folate tracer may be used, it is advantageous to utilize those tracers described and claimed in copending patent application Ser. No. 551,462. More particularly, the folate tracers for use in this invention are preferably a derivative of folic acid comprising folic acid coupled through one or both of its carboxyl groups with the amino nitrogen of a member selected from

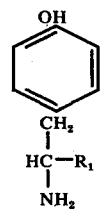 and 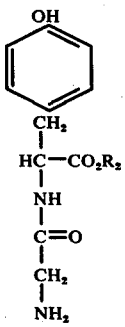

wherein $R_1$ is selected from hydrogen, COOH and $COOR_3$ in which $R_3$ is lower alkyl and $R_2$ is selected from hydrogen and lower alkyl, and wherein said benzene ring is substituted with a gamma emitting isotope (such as $I^{125}$).

The following flow sheet covers a typical assay procedure utilizing all of the improvements of the present invention.

FLOW CHART

A. Set up the tubes as indicated in the first column below (approx. 12 × 75 glass or polypropylene tubes) and add reagents in the order indicated. Use any semi-automatic micropipets which will deliver accurately.

-continued

FLOW CHART

| TUBE | ADD[1] Folate Standard or Patient Sample | ADD[2] Working Tracer Solution | HEAT 15 min. | COOL | ADD[3] Binding Protein Working Solution | INCUBATION 30 min. | ADD[4] Adsorbent Tablets | |
|---|---|---|---|---|---|---|---|---|
| Total Counts Tube | — | 1.0 ml | — | — | — | — | — | Set Aside |
| Blank | 100 ul P-Zero Std. | 1.0 ml | | | 1.0 ml Dist. H$_2$O | | 1 tablet | |
| Zero ng/ml | 100 ul P-Zero Std. | 1.0 ml | Mix | Cool | 1.0 ml | Incubate | 1 tablet | Proceed |
| 1.0 ng/ml | 100 ul P-1.0 Std. | 1.0 ml | gently. | at | 1.0 ml | at | 1 tablet | to |
| 2.5 ng/ml | 100 ul P-2.5 Std. | 1.0 ml | Cap | room | 1.0 ml | room | 1 tablet | steps |
| 5.0 ng/ml | 100 ul P-5.0 Std. | 1.0 ml | or | tem- | 1.0 ml | tempera- | 1 tablet | below. |
| 10.0 ng/ml | 100 ul P-10.0 Std. | 1.0 ml | cover | pera- | 1.0 ml | ture. | 1 tablet | |
| 20.0 ng/m. | 100 ul P-20.0 Std. | 1.0 ml | tubes | ture. | 1.0 ml | | 1 tablet | |
| Patient Sample | 100 ul Patient Sample | 1.0 ml | loosely. | | 1.0 ml | | 1 tablet | |

B. Allow to stand about 5 minutes. Vortex each tube about 10 seconds. Allow to stand about 5 minutes.
C. Centrifuge 10 minutes at 2000–3000 RPM. Decant into counting vials.
D. Count supernates and total counts tube.

[1]PGA (pteroylglutamic acid) was spiked to folate free serum (or serum protein base) at 0, 1, 2.5, 10, 20 ng/cc level.
[2]About 100,000 cpm of iodinated tyramine derivative of PGA in 1 cc, 0.05 M borate, 0.2% (W/V) dithiothreitol, 0.85% (W/V) NaCl buffer, pH 9.4.
[3]About 40 ug to 70 ug of β-lactoglobulin in 1 cc 0.002% merthiolate, 0.1% HSA in H$_2$O.
[4]Typically 80 mg tablet contains 10 mg dextran coated charcoal + 70 mg cellulose.

The following steps more specifically describe the use of the above flow sheet:

1. Label two 12 × 75 mm reaction tubes for the blank, two for each standard including Zero, and two for each sample.
2. To the blank tubes add 100 ul P-Zero standard. To the standard tubes add 100 ul of the appropriate standard— P-Zero, P-1.0, P-2.5, P-5.0, P-10.0 and P-20.0. Add 100 ul of each patient sample to the appropriate patient tubes.
3. To all tubes add 1.0 ml of Working Tracer (Note 2, Flow Chart) Solution. Prepare immediately prior to the assay. Mix all tubes gently.
4. Prepare a total counts tube by adding 1.0 ml Working Tracer Solution to a counting vial. Set aside until Step 11.
5. Place the tube rack containing all of the tubes in a boiling water bath for 15 minutes. Cap or cover tubes loosely. Cool to room temperature by placing in a cold water bath.
6. To the blank add 1.0 ml of distilled water. To all tubes except the blank add 1.0 ml of Folate Binding Protein Working Solution (Note 3, Flow Chart) Mix all tubes well.
7. Incubate at room temperature for 30 minutes.
8. At the end of the incubation period, add one Adsorbent Tablet to each tube, allow to stand about 5 minutes. Vortex each tube for approximately 10 seconds. Allow to stand about 5 minutes.
9. Centrifuge all tubes about 10 minutes at about 2000–3000 RPM to pack the adsorbent.
10. Decant the supernatants into appropriately labelled counting vials.
11. Count each supernatant and the total counts tube. Record the counts.

Utilizing the above procedure a typical calculation may be made as follows with the results graphically displayed in the accompanying drawing.

1. Subtract the average net cpm of the blank from the net cpm of the standards and patient samples to obtain corrected cpm.
   B = corrected cpm for each standard or sample tube.
   T = cpm of the total counts tube.
2. Divide the corrected cpm of each standard and patient sample (B) by the cpm of the total counts tube (T). Multiply this quotient by 100 to obtain the percentage of bound labelled folate as a function of the total counts T(% B/T).
3. Plot each of the standards on linear graph paper, with % B/T on the Y axis, against concentration of folate in ng/ml on the X axis. Draw a smooth curve through the standard points plotted. See FIG. 1.
4. Convert the % B/T values of the patient samples into ng/ml folate using the curve constructed in (3).

EXAMPLE

| Tube | Uncorrected CPM | Corrected CPM | Average Corr. CPM | $\frac{B}{T} \times 100$ | Sample Value Folate ng/ml |
|---|---|---|---|---|---|
| Blank | 6169 6238 | Avg. = 6204 | 0 | — | — |
| P-Zero Std. | 50781 50643 | 44577 44439 | — | 66.9 66.7 | — |
| P-1 Std. 1 ng/ml | 43527 43220 | 37323 37016 | — | 56.0 55.5 | — |
| P-2.5 Std. 2.5 ng/ml | 29284 28733 | 23080 22529 | — | 34.6 33.8 | — |
| P-5.0 Std. 5.0 ng/ml | 19607 19291 | 13403 13087 | — | 20.1 19.6 | — |
| P-10.0 Std. 10.0 ng/ml | 13200 13444 | 6996 7240 | — | 10.5 10.9 | — |
| P-20.0 Std. 20.0 ng/ml | 10021 9455 | 3817 3251 | — | 5.7 4.9 | — |
| Sample | 34641 34998 | 28437 28794 | 28616 | 42.9 | 1.7 ng/ml |
| Total Counts | 67669 65657 | 66663 (avg) | | | |

The amount of dithiopolyol stabilizer is subject to some variation. Generally speaking, the stabilizer should be present in the assay solution during heating so as to constitute at least about 0.05% on a weight-to-reaction volume basis. Usually the stabilizer will be present in a range of about 0.05–0.4% on a weight-to-reaction volume basis. Higher concentrations may be used, although there is no particular advantage. At lower concentrations stabilization effectiveness begins to deteriorate and there is some loss of serum folates.

Concentration effectiveness of the present stabilizers has been demonstrated with respect to dithiothreitol. The following table summarizes recovery of N-methyl tetrahydrofolic acid ("THFA") when subjected to the present assay procedure and determined against a PGA standard curve.

| Concentration of the Dithiothreitol present during heating step | % TFHA Recovery at 3 ng/cc level | 6 ng/cc level |
| --- | --- | --- |
| 0.4% (W/V) | 96.7% | 106.7% |
| 0.2% (W/V) | 90% | 101.7% |
| 0.05% (W/V) | 85% | 98.3% |
| 0.01% (W/V) | 60% | 65% |
| None | 46.7% | 51.7% |

With respect to the dextran coated charcoal utilized in the present process a typical preparation of the charcoal in dried form is as follows.

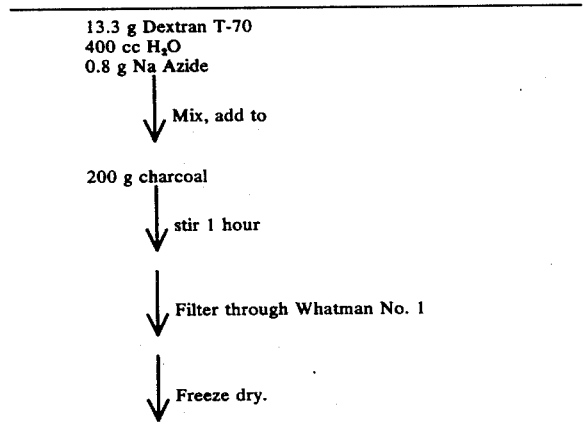

The dried product is then preferably combined with suitable inert binder. A typical material that may be utilized is the commercially available microcrystalline cellulose known as Avicel. Ten mg of the dried dextran coated charcoal are combined with a suitable amount of the cellulose for forming a compressed tablet form. For example, 10 mg of the dextran coated charcoal and 70 mg of Avicel form a tablet of desired physical integrity for use in the present assay method.

What is claimed:

1. In the assay for serum folate by competitive binding in which endogenous serum folate binding proteins are inactivated by heat prior to the competitive binding step, the improvement in which said sera are heated in the presence of a buffered solution containing a stabilizing amount of a dithiopolyol having 4–6 carbon atoms.

2. The improved assay in accordance with claim 1 wherein said dithiopolyol is a 1,4-dithiotetritol.

3. The improved assay in accordance with claim 2 wherein said dithiopolyol is dithiothreitol.

4. The improved assay in accordance with claim 2 wherein said buffered solution is buffered to a pH of about 7.0–10.0.

5. The improved assay in accordance with claim 2 wherein the concentration of said dithiopolyol in said buffered solution in the heating step is at least about 0.05% on a weight-to-reaction volume basis.

6. The improved assay in accordance with claim 5 wherein the concentration of said dithiopolyol in said buffered solution during heating is about 0.05–0.4% on a weight-to-reaction volume basis.

7. An assay for serum folate comprising:
providing a serum sample solution, treating said solution to free serum folate from serum folate binding proteins, inactivating the latter, competitively binding a portion of said serum folate with a folate-selective protein whereby said solution contains bound and free serum folate, adding about 7.5–15 mg for each 0.1 ml of serum sample of dextran coated charcoal in dry solid tablet form to said solution to adsorb free serum folate, and separating said dextran coated charcoal from said solution.

8. The assay in accordance with claim 7 the tablet comprising a compressed combination of dextran coated charcoal and inert binder.

9. The assay in accordance with claim 8 wherein said inert binder is cellulose.

10. An assay for serum folate comprising:
providing a serum sample solution, mixing radioactive folate tracer with said solution, heating said sample solution while stabilized and buffered to a pH of about 7.0–10.0 to free folate from serum folate binding protein, competitively binding a portion of said free folate and radioactive folate tracer with a folate-selective protein, adding about 7.5–15 mg for each 0.1 ml of serum sample of dextran coated charcoal in substantially dry solid tablet form to absorb a portion of free serum folate and free radioactive folate tracer, separating said dextran coated charcoal, and determining folate concentration of said serum sample from the relative amount of radioactive tracer in said solution.

11. An assay for serum folate in accordance with claim 10, the tablet comprising a compressed combination of dextran coated charcoal and cellulose.

12. An assay for serum folate in accordance with claim 10 wherein said buffered solution is heated in the presence of a stabilizing amount of a 1,4-dithiotetritol.

13. An assay for serum folate in accordance with claim 10 wherein said radioactive tracer is a derivative of folic acid comprising folic acid coupled through one or both of its carboxyl groups with the amino nitrogen of a member selected from

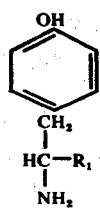 and 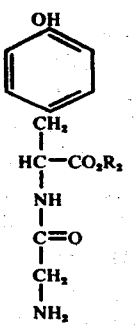

wherein $R_1$ is selected from hydrogen, COOH and $COOR_3$ in which $R_3$ is lower alkyl and $R_2$ is selected from hydrogen and lower alkyl, and wherein said benzene ring is substituted with a gamma emitting isotope.

14. An assay for serum folate in accordance with claim 10 wherein about 10 mg of said dextran coated charcoal is added for each 0.1 ml of serum sample.

15. An assay for serum folate in accordance with claim 13 wherein said gamma emitting isotope is $I^{125}$.

* * * * *